United States Patent [19]

Nakanishi et al.

[11] 4,046,780

[45] Sept. 6, 1977

[54] PREPARATION OF PHTHALIC ANHYDRIDE

[75] Inventors: Yoshiyuki Nakanishi, Minoo; Shigeru Nakamura, Takatsuki; Tetsuji Ono, Amagasaki, all of Japan

[73] Assignee: Nippon Shokubai Kagaku Kogyo Co., Ltd., Osaka, Japan

[21] Appl. No.: 626,913

[22] Filed: Oct. 29, 1975

[51] Int. Cl.$^2$ .......................................... C07D 307/89
[52] U.S. Cl. .................................. 260/346.4; 252/435
[58] Field of Search ...................................... 260/346.4

[56] References Cited

U.S. PATENT DOCUMENTS

| | | | |
|---|---|---|---|
| 1,809,752 | 6/1931 | Jaeger | 260/346.4 |
| 2,142,678 | 1/1939 | Porter | 260/346.4 |
| 3,232,955 | 2/1966 | Nonnenmacher et al. | 260/346.4 |
| 3,909,457 | 9/1975 | Friedrichsen et al. | 260/346.4 X |
| 3,926,846 | 12/1975 | Ono et al. | 260/346.4 X |

*Primary Examiner*—Henry R. Jiles
*Assistant Examiner*—Bernard Dentz
*Attorney, Agent, or Firm*—Wenderoth, Lind & Ponack

[57] ABSTRACT

A method for preparing phthalic anhydride by the catalytic vapor phase oxidation of either ortho-xylene or naphthalene, which comprises passing a gas comprising a molecular oxygen, an inert gas and a member of the group consisting of ortho-xylene and naphthalene first through a catalyst A comprising a catalytically active substance on a porous inert carrier, said catalytically active substance consisting essentially of 1 to 20 parts by weight of $V_2O_5$, 99 to 80 parts by weight of anatase-type $TiO_2$, and, based on the total weight of $V_2O_5$ and $TiO_2$, 0.01 to 1.0% by weight of $Nb_2O_5$, 0.5 to 1.1% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said porous inert carrier comprising essentially SiC, and thereafter through a catalyst B comprising a catalytically active substance on a porous inert carrier, said catalytically active substance consisting essentially of 1 to 20 parts by weight of $V_2O_5$, 99 to 80 parts by weight of anatase-type $TiO_2$, and, based on the total weight of the $V_2O_5$ and $TiO_2$, 0.01 to 1.0% by weight of $Nb_2O_5$, 1.2 to 2.5% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said porous inert carrier comprising essentially SiC.

9 Claims, No Drawings

PREPARATION OF PHTHALIC ANHYDRIDE

This invention relates to a new catalyst to be used in the preparation of phthalic anhydride by the catalytic vapor phase oxidation of either ortho-xylene or naphthalene, as sell as an effective method for its use.

In the conventional process for the preparation of phthalic anhydride by the fixed bed catalytic vapor phase oxidation of ortho-xylene or naphthalene, the reaction was carried out while maintaining the concentration of the starting gas at below the explosion limit, for example, by holding the concentration of ortho-xylene at below 25 liters of air per gram of ortho-xylene in the case of phthalic anhydride production from ortho-xylene. Hence, the volume of the starting gas becomes great, with the consequence that a blower of greater capacity must be used for conveying the gas to the reactor. However, in recent years demands for simplification of the various chemical plants or the saving of auxiliary energy have arisen in various quarters. In the field of preparing phthalic anhydride, there also is a trend to seek a reduction in the volume of the starting gas by a marked enhancement of the concentration of the starting material as compared with the conventional practice thereby simplifying the apparatus employed and reducing the amount of the auxiliary energy required.

However, the reactions of oxidizing ortho-xylene and naphthalene to phthalic anhydride are in both cases violent exothermic reactions. Hence, the catalysts which were suitable for the conventional so-called low gas concentration process cannot necessarily be considered as being equally suitable for the high gas concentration process. For example, in Japanese Patent Publication Nos. 41036/74 and 41271/74 there are disclosed catalysts comprising an active substance consisting predominantly of $V_2O_5$ and $TiO_2$ and supplementally of $Nb_2O_5$, $P_2O_5$, $K_2O$ and/or $Cs_2O$ supported on a porous carrier predominantly of SiC. However, when the reaction is carried out by packing these catalysts in a reaction tube having an inside diameter of 15-30 millimeters and passing orthoxylene therethrough at a concentration of the order of 10-20 liters of air per gram of ortho-xylene, the phthalic anhydride can only be obtained at an extremely low yield. Moreover, there is a marked degradation of the catalyst with the passage of time owing to the great heat load. Hence, these catalysts cannot be used in the high gas concentration processes. This likewise applies in the case of the known catalysts that have been disclosed in German Pat. Nos. 1,442,590 and 2,106,796 and Japanese Laid-Open Pat. No. 5661/72.

It is therefore a primary object of the present invention to provide a catalyst having good selectivity even under high load conditions.

Another object of the invention is to provide a catalyst having a satisfactory thermal durability such as will enable it to endure for a prolonged period of time when used in a continuous oxidation reaction.

According to our studies it was noted that a striking improvement in the thermal stability of the catalyst could be achieved by incorporating $Na_2O$ in the active substances of the aforementioned known catalyst comprising the active substance of $V_2O_5$, $TiO_2$, $Nb_2O_5$, $P_2O_5$, $K_2O$ and/or $Cs_2O$ supported on a porous carrier predominantly of SiC. However, although this $Na_2O$-incorporated $V_2O_5$-$TiO_2$ type supported catalyst possesses such an excellent property, the yield in which it provides the intended phthalic anhydride cannot be regarded as being of sufficiently high level. For instance, when this catalyst is used and ortho-xylene is oxidized at a concentration of 25-26 liters of air per gram of ortho-xylene, the phthalic anhydride can only be obtained at a yield of the order of 108 - 111 weight %. Thus, when considered from the standpoint of its selectivity, it could not qualify as a commercial catalyst. Accordingly, we furthered our researches with a view to making the most of the excellent properties of this catalyst and, as a consequence, we made the following discovery. That is, when the catalyst packed layer was divided into a plurality of layers, for example, two layers, and the layer at the starting gas entry side was packed with a catalyst whose content of $P_2O_5$ was relatively small, while the layer at the reaction gas outlet side was packed with a catalyst whose content of $P_2O_5$ was greater than that of the catalyst used at the starting gas entry side, the peak temperature in the catalyst packed layer was checked to result in a marked improvement in the selectivity of the catalyst and, moreover, the catalyst activity could be stably maintained over a very long period of time even when the reaction was operated under high load conditions such as using the starting gas at much higher concentrations than in the case of the conventional processes.

Thus, there is provided in accordance with the present invention a method for preparing phthalic anhydride which comprises passing a gas consisting of a molecular oxygen, an inert gas and either ortho-xylene or naphthalene first through a layer of a catalyst A comprising a catalytically active substance consisting essentially of 1 to 20 parts by weight of $V_2O_5$ and, correspondingly, 99 to 80 parts by weight of anatase-type $TiO_2$, and, based on the total weight of $V_2O_5$ and $TiO_2$, 0.01 to 1.0%, by weight of $Nb_2O_5$, 0.5 to 1.1% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, supported on a porous inert carrier, and thereafter passing said gas through a layer of a catalyst B comprising a catalytically active substance consisting essentially of 1 to 20 parts by weight of $V_2O_5$ and, correspondingly, 99 to 80 parts by weight of anatase-type $TiO_2$, and, based on the total weight of the $V_2O_5$ and $TiO_2$, 0.01 to 1.0% by weight of $Nb_2O_5$, 1.2 to 2.5% by weight of $P_2O_5$0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, supported on a porous inert carrier.

As indicated hereinabove, it is indispensable in this invention that the content of $P_2O_5$ in the catalyst B is greater than that in the catalyst A. However, as regards the components other than $P_2O_5$ contained in the catalysts A and B, their amounts can be optionally varied within the ranges indicated above.

The anatase-type $TiO_2$ used in preparing the catalytically active substance should preferably be a powder consisting of particles not greater than 1.0 micron in particle diameter, moreover at least 80%, and particularly at least 90%, being those having a diameter not greater than 0.4 micron.

The commercially available anatase-type $TiO_2$ can be used provided that the foregoing conditions are satisfied. However, at times, depending upon the process of its preparation and the starting ore used, trace amounts of compounds of such elements as Fe, Zn, Al, Mn, Cr, Sb, Ca, Pb, etc. are mixed therein. These impurities must not exceed 0.5% by weight of the $TiO_2$, calculated as oxides.

The sources of $V_2O_5$, $Nb_2O_5$, $P_2O_5K_2O$, $Cs_2O$, $Na_2O$ and $Rb_2O$, the other components making up the catalytically active substance, are not limited to the oxides but can be suitbly chosen from those substances which are transformed to such oxides as indicated hereinbefore by heating, such as the ammonium salts, nitrates, organic acid salts, sulfates, halides and hydroxides.

By the expression porous inert carrier, as used in this invention, is meant the porous carrier consisting predominantly of silicon carbide (SiC). Specifically, mentioned can be made of such a porous substance as that in which the aluminum content, calculated as aluminum oxide ($Al_2O_3$), is not more than 10% by weight, and preferably not more than 5% by weight, and the SiC content is at least 50% by weight, preferably at least 80% by weight, and whose apparent porosity (hereinafter referred to as merely porosity) is at least 10%, and preferably 15–45%. A typical example of this carrier is that prepared by self-sintering SiC having a purity of above 98% until one having a porosity of 15–40% is obtained. While there is imposed no particular restriction as to the configuration of the carrier as long as its diameter is 2–15 millimeters, those of spherical or cylindrical shape are convenient as far as their handling is concerned.

The catalysts A and B can be prepared in customary manner. However, as in the case with the catalyst disclosed in Japanese Patent Publication No. 41036/74, these catalysts must be so prepared that, of the pores contained in the supported catalytically active substance, the pore volume of pores of diameters 0.15 – 0.45 micron must account for at least 70%, and particularly at least 80%, of the pore volume of pores of diameter 10 microns or less. For accomplishing this, the preparation of the catalytically active substance must be carried out with a slurry concentration of 5–25%, and preferably 10–20%, when an anatase-type $TiO_2$ of an average particle size of 0.005 – 0.05 micron is used, and with a slurry concentration of 10 – 40%, and preferably 15 – 25%, when an anatase-type $TiO_2$ of average particle size of 0.05 – 0.4 micron is used. In either case this catalyst slurry should be thoroughly mixed and homogenized with an emulsifier.

While the rate of deposition of the catalytically active substance on the carrier will vary depending upon the carrier used and its configuration, a deposition rate of 3–15 grams of the catalytically active substance per 100 cubic centimeters of the carrier is suitable.

The catalyst obtained in this manner is then calcined for 2–10 hours at 300°– 600° C., and preferably 500°– 550° C., under passage of air, after which the resulting catalyst is packed in a reaction tube, e.g., a vertical reaction tube having a length of 1–5 meters and an inside diameter of 15 – 40 millimeters, where it is used to carry out the reaction. In packing the catalyst there is the necessity, however, of giving consideration to ensure that the packed layer of catalyst A is disposed at the starting gas entry side of the reaction tube, while the packed layer of catalyst B is disposed at the reaction gas outlet side of the reaction tube. And in this case it is especially preferred that the two packed layers should be disposed adjoining each other and that the packed lengths (volumes) of the catalysts A and B account for respectively 30 – 70% and 70 – 30% of the packed portion of the reaction tube.

The catalyst-packed layer, instead of being divided into two layers of different compositions, may, if necessary, be divided into three or more layers of different compositions. Needless to say, consideration must however be given to ensure that the content of $P_2O_5$ of the packed layer located close to the entry side of the reaction tube is the smallest, while the packed layer located at the middle part of the tube contains the $P_2O_5$ in a medium amount.

While the catalyst of this invention can also be employed in the reaction for preparing carboxylic acids or carboxylic acid anhydrides by the catalytic vapor phase oxidation of such aromatic hydrocarbons as benzene and durene, it is most suitably used for preparing phthalic anhydride by the catalytic vapor phase oxidation of ortho-xylene or naphthalene. In carrying out the reaction for preparing phthalic anhydride, the conditions employed are as follows: a temperature of 310°– 420° C. (the temperature of the heat transfer medium, which will hereinafter be abbreviated to NT), a gas concentration (GC) of 15–40 liters-air/gram-ortho-xylene, and a space velocity (SV) of 1000 – 8000 $hr^{-1}$ (NTP). More specifically, when the starting material is ortho-xylene, the reaction is carried out under the conditions of NT of 330°– 420° C., especially 350°– 400° C., GC of 15–40, especially 15–30 liters-air/gram-ortho-xylene, and SV of 1000 – 6000, especialy 2000 – 4500 $hr^{-1}$ (NTP). In this case, the phthalic anhydride is obtained from the time immediately subsequent to the start of the reaction at an extremely high yield of 110 – 118% by weight without hardly any decline in the yield even when the reaction is continuously operated over a prolonged period of time. On the other hand, when the starting material is naphthalene, the reaction is carried out under the conditions of NT of 310° – 400° C., especially 330°– 390° C., GC of 15 –40, especially 15 – 30 liters-air/gram-naphthalene, and SV of 2000 – 8000, especially 2000 – 6000 $hr^{-1}$ (NTP). In this case, the phthalic anhydride is obtained at a yield of 100 – 105% by weight from the time immediately subsequent to the start of the reaction, and the catalyst exhibits a very stable activity over a prolonged period of time.

According to this invention, the incorporation of $Na_2O$ in the $V_2O_5$-$TiO_2$-containing supported catalyst results in a marked improvement in the durability of the catalyst. Further, as a consequence of having varied the content of $P_2O_5$ in the catalytically active substance in accordance with the position of the packed layer, a further great improvement of the durability of the catalyst is achieved. There is also a marked enhancement of the selectivity and loading property of the catalyst. In addition, as a consequence of having developed a catalyst such as described, it becomes possible to greatly reduce the scale of the reaction apparatus as a whole, with the consequence that equipment cost as well as the running costs can be greatly reduced.

The following examples and comparative examples will serve to more fully illustrate the present invention.

EXAMPLE 1

A 60% aqueous titanium tetrachloride solution was prepared by slowly adding dropwise 5700 grams of special reagent grade titanium tetrachloride ($TiCl_4$) to water, after which 2940 grams of special reagent grade sulfuric acid was added to the resulting aqueous titanium tetrachloride solution with stirring. Separately, a saturated aqueous solution containing 3940 grams of special reagent grade ammonium sulfate heated at 100° C. was prepared. This saturated aqueous solution was added to the foregoing aqueous $TiCl_4$-$H_2SO_4$ solution with stirring. After completion of the addition, the combined solution was left to stand, whereupon was precipitated ammonium titanyl sulfate $(NH_4)_2SO.TiOSO_4.H_2O$. After this precipitate was separated by filtration, it was calcined for 3 hours at 900° C. to obtain an anatase-tupe $TiO_2$ of average particle size of 0.25 micron.

An aqueous oxalic acid solution was prepared by dissolving 50 grams of oxalic acid in 3000 cc of deionized water, to which were then added with thorough stirring 23.6 grams of ammonium metavanadate, 4.66 grams of niobium chloride, 15.17 grams of ammonium dihydrogen phosphate, 1.64 grams of potassium hydroxide and 1.57 grams of sodium carbonate.

To the so obtained aqueous solution was then added 900 grams of the aforesaid $TiO_2$ followed by thorough emulsification for 30 minutes with an emulsifier to prepare a catalyst slurry.

In a stainless steel rotary kiln of a length of 80 centimeters and an inside diameter of 35 centimeters capable of being heated from the outside were placed 1000 cc of spherical carriers of self-sintered Sic (SiC purity 99%) of a diameter of 6 millimeters and a porosity of 35%. After having preheated the carriers at 200°- 250° C., the foregoing slurry was sprayed onto the carriers while rotating the rotary kiln to effect the deposition of 80 grams of the catalytically active substance. The carrier-supported catalyst was then calcined for 6 hours at 550° C. while passing air therethrough.

The ratio by weight of the catalytically active substances contained in this catalyst was $V_2O_5:TiO_2:Nb_2O_5:P_2O_5:K_2O:Na_2O = 2:98:0.25:1.02:0.15:0.1$. When this catalyst was measured for its pore distribution with a mercury porosimeter (Winslow porosimeter, Aminco), the pore volume of pores having diameters 0.15–0.45 micron accounted for 88% of the total pore volume of the pores of diameters 10 microns or less. This is designated catalyst A.

Next, when preparing the catalyst B, the operation was carried out exactly as in the case with the preparation of the catalyst A but using the ammonium dihydrogen phosphate is an amount of 19.34 grams in preparing the aforementioned catalyst slurry. A catalyst was obtained having a ratio by weight of the catalytically active substances of $V_2O_5:TiO_2:Nb_2O_5:P_2O_5:K_2O:Na_2O = 2:98:0.25:1.3:0.15:0.1$ and in which the pore volume of the pores of diameters 0.15 - 0.45 micron accounted for 87% of the total pore volume of the pores of diameters 10 microns or less. As indicated above, this is designated catalyst B.

Three vertical stainless steel reaction tubes (Nos. 1–3) having an inside diameter of 27 millimeters and a length of 3 meters were each packed first with the catalyst B to a height of 1.25 meters and then atop thereof with the catalyst A to a height of 1.25 meters. Air containing ortho-xylene in varying concentrations was then passed through the several reaction tubes from the top thereof.

The reaction conditions of the reaction tubes and the results obtained are shown in Table 1. The ortho-xylene used was of 99% purity, and the yield of the phthalic anhydride was that reduced to a purity basis.

Table 1

| Reaction Tube | Time Elapsed | NT (° C) | SV (hr$^{-1}$) | GC (l/g) | Phathalic anhydride yield (wt.%) |
|---|---|---|---|---|---|
| No. 1 | Initial stage | 370 | 3500 | 25.5 | 117.7 |
|  | After 3 months | 370 | 3500 | 25.5 | 117.8 |
|  | After 6 months | 370 | 3500 | 25.5 | 117.5 |
| No. 2 | Initial stage | 370 | 3500 | 20.0 | 116.9 |
|  | After 3 months | 370 | 3500 | 20.0 | 116.4 |
|  | After 6 months | 372 | 3500 | 20.0 | 116.6 |
| No. 3 | Initial stage | 370 | 3500 | 16.6 | 114.3 |
|  | After 3 months | 373 | 3500 | 16.6 | 113.9 |
|  | After 6 months | 375 | 3500 | 16.6 | 113.6 |

EXAMPLE 2

Catalysts A and B such as described hereinbelow were prepared by following the procedures described in Example 1, using as the catalyst starting materials ammonium metavanadate, the $TiO_2$ obtained in Example 1, niobium chloride, ammonium dihydrogen phosphate, potassium sulfate, rubidium sulfate and sodium carbonate and, as the carrier, a shaped carrier (sphere of 5-mm diameter) of SiC having a porosity of 42% consisting of 2% by weight of $Al_2O_3$, 92% by weight of SiC and the remainder of $SiO_2$. By the expression "pore volume rate," as used hereinbelow and hereinafter, is meant the percentage of the volume of pores of diameters 0.15 - 0.45 micron to the total pore volume of pores of diameters 10 micron or less.

| Catalyst | Composition (wt. ratio) | | | | | | Pore Volume Rate (%) |
|---|---|---|---|---|---|---|---|
|  | $V_2O_5$ | $TiO_2$ | $Nb_2O_5$ | $P_2O_5$ | $K_2O$ | $Rb_2O$ : $Na_2O$ |  |
| A | 2 | 98 | 0.5 | 0.8 | 0.05 | 0.3 : 0.05 | 87 |
| B | 2 | 98 | 0.5 | 1.4 | 0.05 | 0.3 : 0.05 | 87 |

Three vertical stainless steel reaction tubes (Nos. 1–3) having an inside diameter of 27 millimeters and a length of 2 meters were each packed first with the catalyst B to a height of 0.7 meters and then atop thereof with the catalyst A to a height of 1.1 meters. The performances of the catalysts were then tested by operating as in Example 1, with the results shown in Table 2.

Table 2

| Reaction Tube | Time Elapsed | NT (° C) | SV (hr$^{-1}$) | GC (l/g) | Phthalic anhydride yield (wt.%) |
|---|---|---|---|---|---|
| No.1 | Initial stage | 375 | 3700 | 25.5 | 117.4 |
|  | After 3 months | 375 | 3700 | 25.5 | 117.2 |
|  | After 6 months | 375 | 3700 | 25.5 | 117.0 |
| No.2 | Initial stage | 372 | 3500 | 20.5 | 116.7 |
|  | After 3 months | 372 | 3500 | 20.5 | 116.8 |
|  | After 6 months | 375 | 3500 | 20.5 | 116.3 |
|  | Initial stage | 370 | 3500 | 16.7 | 115.9 |

Table 2-continued

| Reaction Tube | Time Elapsed | NT (°C) | SV (hr$^{-1}$) | GC (l/g) | Phthalic anhydride yield (wt.%) |
|---|---|---|---|---|---|
| No.3 | After 3 months | 373 | 3500 | 16.7 | 116.0 |
|  | After 6 months | 378 | 3500 | 16.7 | 116.1 |

EXAMPLE 3

Catalysts A and B such as described hereinbelow were prepared by following the procedures described in Example 1, using as the catalyst starting materials ammonium metavanadate, anatase-type $TiO_2$ for pigment use of average particle size of 0.28 micron (containing 900 ppm of $K_2O$, 2200 ppm of $P_2O_5$, 3000 ppm of $Nb_2O_5$ and trace amounts of other substances), cesium sulfate, ammonium dihydrogen phosphate and sodium carbonate and, as the carrier, a spherical carrier or self-sintered Sic (SiC purity 99%) of 5-mm diameter and 30% porosity.

| Catalyst | Composition (wt. ratio) | | | | | | Pore volume Rate (%) |
|---|---|---|---|---|---|---|---|
| A | $V_2O_5$:3 | $TiO_2$:97 | $Nb_2O_5$:0.3 | $P_2O_5$:1.0 | $K_2O$:0.09 | $Cs_2O$:0.12 | $Na_2O$:0.1 | 89 |
| B | $V_2O_5$:2 | $TiO_2$:98 | $Nb_2O_5$:0.3 | $P_2O_5$:1.3 | $K_2O$:0.09 | $Cs_2O$:0.12 | $Na_2O$:0.1 | 89 |

Three vertical stainless steel reaction tubes (Nos. 1-3) having an inside diameter of 27 millimeters and a length of 3 meters were each packed first with catalyst B and then with catalyst A to a total height of 2.5 meters with the packed heights of the two catalysts having a ratio of 1:1. Tests were then conducted as in Example 1, with the results shown in Table 3.

Table 3

| Reaction Tube | Time Elapsed | NT (°C) | SV (hr$^{-1}$) | GC (l/g) | Phthalic anhydride yield (wt.%) |
|---|---|---|---|---|---|
| No.1 | Initial stage | 365 | 3200 | 25.5 | 118.3 |
|  | After 3 months | 365 | 3200 | 25.5 | 118.4 |
|  | After 6 months | 365 | 3200 | 25.5 | 118.4 |
| No.2 | Initial stage | 365 | 3200 | 20.0 | 117.8 |
|  | After 3 months | 365 | 3200 | 20.0 | 117.5 |
|  | After 6 months | 365 | 3200 | 20.0 | 117.0 |
| No.3 | Initial stage | 365 | 3200 | 16.5 | 117.3 |
|  | After 3 months | 367 | 3200 | 16.5 | 116.7 |
|  | After 6 months | 370 | 3200 | 16.5 | 116.2 |

EXAMPLE 4

The ammonium titanyl sulfate obtained in Example 1 was heat-treated for 5 hours at 800° C. to obtain an anatase-type $TiO_2$ of average particle size of 0.08 micron.

To an aqueous oxalic acid solution obtained by dissolving 210 grams of oxalic acid in 3600 cc of deionized water were added 100.6 grams of ammonium metavanadate, 4.0 grams of niobium chloride, 9.51 grams of ammonium dihydrogen phosphate, 0.81 gram of potassium hydroxide, 1.68 grams of rubidium sulfate and 0.83 gram of sodium carbonate, and the mixture was thoroughly stirred. To this was then added 900 grams of the aforesaid $TiO_2$, after which the operation was carried out as in Example 1 to obtain a catalyst slurry. This slurry was sprayed as in Example 1 onto 1000 cc of irregular shaped carriers of SiC (SiC purity 98%) crushed to sizes of 5-7 millimeters and having a porosity of 18% to effect the deposition of 85 grams of the catalytically active substance, after which the carrier-supported catalyst was calcined for 85 hours at 530° C. under passage of air to obtain a catalyst A such as described hereinbelow.

Separately, an aqueous oxalic acid solution was obtained by dissolving 210 grams of oxalic acid in 3600 cc of deionized water, to which were then added with thorough stirring 100.6 grams of ammonium metavanadate, 4.0 grams of niobium chloride, 26.9 grams of ammonium dihydrogen phosphate, 2.0 grams of cesium sulfate, 2.1 grams of rubidium sulfate and 2.5 grams of sodium carbonate. Next, to the resulting mixture was added 900 grams of the aforesaid $TiO_2$ to obtain as in Example 1 a catalyst slurry, following which the experiment was carried out exactly as in the case with the preparation of the above catalyst A to prepare a catalyst B such as described below.

| Catalyst | Composition (wt. ratio) | | | | | | | Pore Volume Rate (%) |
|---|---|---|---|---|---|---|---|---|
| A | $V_2O_5$:8 | $TiO_2$:92 | $Nb_2O_5$:0.2 | $P_2O_5$:0.6 | $K_2O$:0.07 | $Rb_2O$:0.12 | $Na_2O$:0.05 | 87 |
| B | $V_2O_5$:8 | $TiO_2$:92 | $Nb_2O_5$:0.2 | $P_2O_5$:1.7 | $Cs_2O$:0.16 | $Rb_2O$:0.15 | $Na_2O$:0.15 | 86 |

Three vertical stainless steel reaction tubes (Nos, 1-3) having an inside diameter of 27 millimeters and a length of 3 meters were each packed first with catalyst B and then with catalyst A to a total height of 2.8 meters with the packed heights of the two catalysts having a ratio of A : B = 6 : 4. Tests were then conducted as in Example 1, with the results shown in Table 4.

Table 4

| Reaction Tube | Time Elapsed | NT (°C) | SV (hr$^{-1}$) | GC (l/g) | Phthalic anhydride yield (wt.%) |
|---|---|---|---|---|---|
| No.1 | Initial stage | 380 | 3000 | 25.5 | 116.5 |
|  | After 3 months | 380 | 3000 | 25.5 | 116.2 |
|  | After 6 months | 380 | 3000 | 25.5 | 116.3 |
| No.2 | Initial stage | 380 | 3000 | 20.0 | 115.7 |
|  | After 3 months | 380 | 3000 | 20.0 | 115.5 |
|  | After 6 months | 380 | 3000 | 20.0 | 115.1 |
| No.3 | Initial stage | 380 | 3000 | 17.0 | 114.5 |
|  | After 3 months | 382 | 3000 | 17.0 | 114.1 |
|  | After 6 months | 386 | 3000 | 17.0 | 113.8 |

EXAMPLE 5

Urea was added in excess to an aqueous TiCl₄ solution, after which the mixture was heated to effect the uniform precipitation of titanium hydroxide. After separating the precipitate by filtration and thoroughn washing in water so as to ensure that no chlorine ions remain, the precipitate was dried and thereafter calcined for 8 hours at 680° C. The calcined product was then pulverized to obtain an anatase-type $TiO_2$ of average particle size of 0.01 micron. 270 Grams of oxalic acid was added to 5100 cc of deionized water to prepare an aqueous oxalic acid solution, to which were then added with thorough stirring 128.6 grams of ammonium metavanadate, 10.1 grams of niobium chloride, 14.6 grams of ammonium dihydrogen phosphate, 2.0 grams of cesium sulfate and 2.56 grams of sodium hydroxide. Next, 900 grams of the aforesaid $TiO_2$ was added to the foregoing mixture followed by operating as in Example 1 to prepare a catalyst slurry. This slurry was then sprayed as in Example 1 onto 1000 cc of carriers of self-sintered SiC of pellet form 5 millimeters in diameter and 5 millimeters in length and having a porosity of 37% of effect the deposition of 80 grams of the catalytically active substance, after which the carrier-supported catalyst was calcined for 10 hours at 500° C. under passage of air to obtain a catalyst A such as described below.

Separately, 410 grams of oxalic acid was added to 5100 cc of deionized water to prepared an aqueous oxalic acid solution, to which were then added with thorough stirring 204 grams of ammonium metavanadate, 15.0 grams of niobium chloride, 20.6 grams of ammonium dihydrogen phosphate, 1.26 grams of potassium hydroxide and 1.23 grams of sodium hydroxide. This was followed by adding 900 grams of the aforesaid $TiO_2$ to obtain as in Example 1 a catalyst slurry, after which the experiment was conducted exactly as in the case with the preparation of the above catalyst A to prepare a catalyst B such as described below.

| Catalyst | Composition (wt. ratio) | | | | | | Pore Volume Rate (%) |
|---|---|---|---|---|---|---|---|
| A | $V_2O_5$: 10: | $TiO_2$: 90: | $Nb_2O_5$: 0.5: | $P_2O_5$: 0.9: | $Cs_2O$: 0.16: | $Na_2O$ 0.15 | 74 |
| B | $V_2O_5$: 15: | $TiO_2$: 85: | $Nb_2O_5$: 0.7: | $P_2O_5$: 1.2: | $K_2O$: 0.1: | $Na_2O$ 0.09 | 73 |

Three vertical stainless steel reaction tubes (Nos. 1–3) having an inside diameter of 27 millimeters and a length of 3 meters were each packed first with catalyst B and then with catalyst A to a total height of 2.5 meters with the packed heights of the two catalysts having a ratio of 1:1. Tests were then conducted as in Example 1, with the results shown in Table 5.

Table 5

| Reaction Tube | Time Elapsed | NT (° C) | SV (hr⁻¹) | GC (l/g) | Phthalic anhydride yield (wt.%) |
|---|---|---|---|---|---|
| No.1 | Initial stage | 375 | 3500 | 25.5 | 114.2 |
| | After 3 months | 375 | 3500 | 25.5 | 114.0 |
| | After 6 months | 375 | 3500 | 25.5 | 113.8 |
| No.2 | Initial stage | 375 | 3500 | 20.0 | 113.8 |
| | After 3 months | 375 | 3500 | 20.0 | 113.8 |
| | After 6 months | 375 | 3500 | 20.0 | 113.6 |
| No.3 | Initial stage | 375 | 3500 | 17.5 | 113.3 |
| | After 3 months | 375 | 3500 | 17.5 | 113.0 |
| | After 6 months | 379 | 3500 | 17.5 | 113.2 |

EXAMPLE 6

The following catalysts A and B were prepared in accordance with the procedure described in Example 1, using as the catalyst starting materials the $TiO_2$ obtained in Example 1, ammonium metavanadate, niobium chloride, ammonium dihydrogen phosphate, cesium sulfate and sodium hydroxide and as the carrier a self-sintered spherical carrier of SiC of a diameter of 8 millimeters and a porosity of 30%.

| Catalyst | Composition (wt. ratio) | | | | | | Pore Volume Rate (%) |
|---|---|---|---|---|---|---|---|
| A | $V_2O_5$: 2: | $TiO_2$: 98: | $Nb_2O_5$: 0.1: | $P_2O_5$: 1: | $Cs_2O$: 0.35: | $Na_2O$ 0.1 | 88 |
| B | $V_2O_5$: 2: | $TiO_2$: 98: | $Nb_2O_5$: 0.1: | $P_2O_5$: 1.2: | $Cs_2O$: 0.26: | $Na_2O$ 0.1 | 88 |

Two vertical stainless steel reaction tubes (Nos. 1–2) having an inside diameter of 32 millimeters and a length of 3.5 meters were each packed first with catalyst B and then catalyst A to a total height of 3 meters with the packed heights of the two catalysts having a ratio of 1 : 1. The reaction results obtained by operating as in Example 1 are shown in Table 6.

Table 6

| Reaction Tube | Time Elapsed | NT (° C) | SV (hr⁻¹) | GC (l/g) | Phthalic anhydride yield (wt.%) |
|---|---|---|---|---|---|
| No.1 | Initial stage | 365 | 3300 | 28.5 | 113.6 |
| | After 3 months | 365 | 3300 | 28.5 | 113.3 |
| | After 6 months | 368 | 3300 | 28.5 | 113.1 |
| No.2 | Initial stage | 365 | 3300 | 23.5 | 112.8 |
| | After 3 months | 367 | 3300 | 23.5 | 112.7 |
| | After 6 months | 373 | 3300 | 23.5 | 112.4 |

EXAMPLE 7

The following two classes of catalysts A and b were prepared by operating as in Example 1, using as the catalyst starting materials ammonium metavanadate, the $TiO_2$ obtained in Example 4, niobium chloride, ammonium dihydrogen phosphate, potassium hydroxide, cesium sulfate and sodium carbonate and as the carrier a 6-mm self-sintered spherical carrier of SiC having a porosity of 35%.

| Catalyst | Composition (wt. ratio) | | | | | | Pore Volume Rate (%) |
|---|---|---|---|---|---|---|---|
| A | $V_2O_5$: 12 | $TiO_2$: 88 | $Nb_2O_5$: 0.4 | $P_2O_5$: 0.7 | $K_2O$: 0.07 | $Cs_2O$: 0.15 | $Na_2O$ 0.08 | 86 |
| B | $V_2O_5$: 12 | $TiO_2$: 88 | $Nb_2O_5$: 0.4 | $P_2O_5$: 1.5 | $K_2O$: 0.08 | $Cs_2O$: 0.12 | $Na_2O$ 0.12 | 86 |

Two vertical stainless steel reaction tubes (Nos. 1–2) having an inside diameter of 27 millimeters and a length of 3 meters, which were immersed in molten salt of 360° C., were each packed first with catalyst B and then with catalyst A to a total height of 2.5 meters with the packed heights having a ratio of 1:1. Air containing naphthalene in varying concentrations was then passed through each tube from the top thereof. The reactions conditions of each tube and the results obtained are shown in Table 7. The naphthalene used was of 98% purity, while the yield of phthalic anhydride is a value reduced to purity basis.

Table 7

| Reaction Tube | Time Elapsed | NT (°C) | SV ($hr^{-1}$) | GC (l/g) | Phthalic anhydride yield (wt.%) |
|---|---|---|---|---|---|
| No.1 | Initial stage | 360 | 4000 | 30 | 105.3 |
| | After 3 months | 360 | 4000 | 30 | 105.1 |
| | After 6 months | 360 | 4000 | 30 | 105.1 |
| No.2 | Initial stage | 360 | 4000 | 22 | 103.8 |
| | After 3 months | 360 | 4000 | 22 | 103.8 |
| | After 6 months | 360 | 4000 | 22 | 103.5 |

EXAMPLE 8

The following two classes of catalysts A and B were prepared by operating as in Example 3, using as the catalyst starting materials ammonium metavanadate, the $TiO_2$ used in Example 3, niobium chloride, ammonium dihydrogen phosphite, potassium sulfate, cesium sulfate, rubidium nitrate and sodium carbonate and as the carrier an irregular shaped carrier of SiC of particle size of 5–7 millimeters and a porosity of 18%.

| Catalyst | Composition (wt. ratio) | | | | | | Pore Volume Rate (%) |
|---|---|---|---|---|---|---|---|
| A | $V_2O_5$: 5 | $TiO_2$: 95 | $Nb_2O_5$: 0.4 | $K_2O$: 0.12 | $Cs_2O$: 0.2 | $Na_2O$: 0.1 | $P_2O_5$ 1.0 | 85 |
| B | $V_2O_5$: 5 | $TiO_2$: 95 | $Nb_2O_5$: 0.4 | $K_2O$: 0.2 | $Cs_2O$: 0.3 | $Na_2O$: 0.1 | $P_2O_5$ 2.2 | 85 |

Two vertical stainless steel reaction tubes (Nos. 1–2) having an inside diameter of 27 millimeters and a length of 2 meters were packed first with catalyst B and then atop thereof with catalyst A to a total height of 1.8 meters with the packed heights of the two catalysts having a ratio of A:B = 6:4. The results of the oxidation reaction obtained by carrying out tests as in Example 7 are shown in Table 8.

Table 8

| Reaction Tube | Time Elapsed | NT (°C) | SV ($hr^{-1}$) | GC (l/g) | Phthalic anhydride yield (wt.%) |
|---|---|---|---|---|---|
| No.1 | Initial stage | 365 | 3800 | 28.0 | 104.6 |
| | After 3 months | 365 | 3800 | 28.0 | 104.3 |
| | After 6 months | 365 | 3800 | 28.0 | 104.3 |
| No.2 | Initial stage | 365 | 3500 | 20.0 | 102.3 |
| | After 3 months | 365 | 3500 | 20.0 | 102.0 |
| | After 6 months | 367 | 3500 | 20.0 | 101.8 |

COMPARATIVE EXAMPLE 1

Two vertical stainless steel reaction tubes (Nos. 1–2) having an inside diameter of 27 millimeters and a length of 3 meters were each packed with the catalyst A obtained in Example 1 to height of 2.5 meters, following which the oxidation reaction of ortho-xylene was carried out as in Example 1. Next, a similar experiment was also carried out with the catalyst B obtained in Example 1. The results obtained in these reactions are shown in Table 9.

Table 9

| Catalyst | Reaction Tube | Time Elapsed | NT (°C) | SV ($hr^{-1}$) | GC (l/g) | Phthalic anhydride yield (wt.%) |
|---|---|---|---|---|---|---|
| A | No.1 | Initial stage | 390 | 3000 | 25.5 | 110.5 |
| | | After 3 months | 390 | 3000 | 25.5 | 110.5 |
| | | After 6 months | 390 | 3000 | 25.5 | 110.6 |
| | No.2 | Initial stage | 385 | 3000 | 16.5 | 103.5 |
| | | After 3 months | 405 | 3000 | 16.5 | 95.0 |
| B | No.1 | Initial stage | 365 | 4000 | 25.5 | 111.3 |
| | | After 3 months | 365 | 4000 | 25.5 | 111.0 |
| | | After 6 months | 365 | 4000 | 25.5 | 111.2 |
| | No.2 | Initial stage | 365 | 3500 | 16.5 | 103.0 |
| | | After 3 months | 395 | 3500 | 16.5 | 97.0 |

COMPARATIVE EXAMPLE 2

An experiment was carried out as in Comparative Example 1, using the catalysts A and B obtained in Example 4. The results obtained are shown in Table 10.

Table 10

| Catalyst | Reaction Tube | Time Elapsed | NT (°C) | SV ($hr^{-1}$) | GC (l/g) | Phthalic anhydride yield (wt.%) |
|---|---|---|---|---|---|---|
| A | No.1 | Initial stage | 400 | 3000 | 25.5 | 109.8 |
| | | After 3 months | 400 | 3000 | 25.5 | 109.5 |
| | | After 6 months | 400 | 3000 | 25.5 | 109.5 |
| | No.2 | Initial stage | 400 | 3000 | 17.5 | 101.5 |
| | | After 3 months | 430 | 3000 | 17.5 | 94.3 |

Table 10-continued

| Catalyst | Reaction Tube | Time Elapsed | NT (°C) | SV (hr⁻¹) | GC (l/g) | Phthalic anhydride yield (wt.%) |
|---|---|---|---|---|---|---|
| B | No.1 | Initial stage | 370 | 3600 | 25.5 | 110.1 |
|   |      | After 3 months | 370 | 3600 | 25.5 | 110.2 |
|   |      | After 6 months | 370 | 3600 | 25.5 | 110.1 |
|   | No.2 | Initial stage | 370 | 3300 | 17.5 | 102.5 |
|   |      | After 3 months | 395 | 3000 | 17.5 | 95.8 |

EXAMPLE 9

Example 3 was repeated, except that the oxidation reaction of ortho-xylene was carried out with varied packed height ratios of catalyst A to catalyst B. The results obtained are shown in Table 11.

Table 11

| A : B | NT (°C) | SV (hr⁻¹) | GC (l/g) | Phthalic anhydride yield (wt.%) |
|---|---|---|---|---|
| 2 : 8 | 365 | 3500 | 25.5 | 111.5 |
| 4 : 6 | 365 | 3500 | 25.5 | 115.1 |
| 5 : 5 | 365 | 3200 | 25.5 | 118.3 |
| 6 : 4 | 370 | 3200 | 25.5 | 116.1 |
| 8 : 2 | 385 | 3000 | 25.5 | 110.6 |

EXAMPLE 10

Example 9 was repeated but using the catalyst obtained in Example 4. The results obtained are shown in Table 12.

Table 12

| A : B | NT (°C) | SV (hr⁻¹) | GC (l/g) | Phthalic anhydride yield (wt.%) |
|---|---|---|---|---|
| 2 : 8 | 370 | 3000 | 25.5 | 111.0 |
| 4 : 6 | 375 | 3000 | 25.5 | 114.3 |
| 5 : 5 | 380 | 3000 | 25.5 | 116.1 |
| 6 : 4 | 380 | 3000 | 25.5 | 116.5 |
| 8 : 2 | 390 | 3000 | 25.5 | 111.9 |

EXAMPLE 11

Example 1 was repeated but varying the $P_2O_5$ contents of the catalysts A and B. The results obtained are shown in Table 13.

Table 13

| Catalyst Composition (wt. ratio) $V_2O_5:TiO_2:Nb_2O_5:P_2O_5:K_2O:Na_2O$ | NT (°C) | SV (hr⁻¹) | GC (l/g) | Phthalic anhydride yield (wt.%) |
|---|---|---|---|---|
| Catalyst A, 2 : 98 : 0.25 : 0.4 : 0.15 : 0.1<br>Catalyst B, 2 : 98 : 0.25 : 1.3 : 0.15 : 0.1 | 390 | 3000 | 25.5 | 110.2 |
| Catalyst A, 2 : 98 : 0.25 : 1.2 : 0.15 : 0.1<br>Catalyst B, 2 : 98 : 0.25 : 1.3 : 0.15 : 0.1 | 370 | 3500 | 25.5 | 112.6 |
| Catalyst A, 2 : 98 : 0.25 : 1.02: 0.15 : 0.1<br>Catalyst B, 2 : 98 : 0.25 : 2.0 : 0.15 : 0.1 | 368 | 3500 | 25.5 | 116.0 |
| Catalyst A, 2 : 98 : 0.25 : 1.02 : 0.15 : 0.1<br>Catalyst B, 2 : 98 : 0.25 : 0.3 : 0.15 : 0.1 | 365 | 3500 | 25.5 | 110.5 |
| Catalyst A, 2 : 98 : 0.25 : 1.02 : 0.15 : 0.1<br>Catalyst B, 2 : 98 : 0.25 : 1.0 : 0.15 : 0.1 | 390 | 3000 | 25.5 | 110.3 |

COMPARATIVE EXAMPLE 3

The following two classes of catalysts A and B were prepared by the procedure described in Example 1, using as the catalyst starting materials ammonium metavanadate, the $TiO_2$ obtained in Example 1, niobium chloride, ammonium dihydrogen phosphate, potassium hydroxide and rubidium sulfate and as the carrier a 6 millimeters spherical carrier of self-sintered SiC of a porosity of 35%.

| Catalyst | Composition (wt. ratio) | | | | | | Pore Volume Rate (%) |
|---|---|---|---|---|---|---|---|
|   | $V_2O_5$: | $TiO_2$: | $Nb_2O_5$: | $P_2O_5$: | $K_2O$: | $Rb_2O$ |   |
| A | 2 : | 98 : | 0.25: | 1.0: | 0.15: | 0.28 | 89 |
| B | 2 : | 98 : | 0.25: | 1.2: | 0.15: | 0.28 | 89 |

Two vertical stainless steel reaction tubes (Nos. 1–2) having an inside diameter of 27 millimeters and a length of 3 meters were each packed first with catalyst B and then atop thereof with catalyst A to a total height of 2.5 meters with the packed heights of the two catalysts having a ratio of 1:1. The oxidation reaction of ortho-xylene was then carried out as in Example 1, with the results shown in Table 14.

Table 14

| Reaction Tube | Time Elapsed | NT (°C) | SV (hr⁻¹) | GC (l/g) | Phthalic anhydride yield (wt.%) |
|---|---|---|---|---|---|
| No.1 | Initial stage | 375 | 3500 | 25.5 | 117.2 |
|      | After 3 months | 377 | 3500 | 25.5 | 116.2 |
|      | After 6 months | 383 | 3500 | 25.5 | 115.4 |
| No.2 | Initial stage | 375 | 3500 | 16.6 | 114.4 |
|      | After 3 months | 382 | 3500 | 16.6 | 113.2 |
|      | After 6 months | 390 | 3500 | 16.6 | 112.0 |

What we claim:

1. A method for preparing phthalic anhydride by catalytic vapor phase oxidation of ortho-xylene or naphthalene, which comprises passing a gas mixture comprising molecular oxygen, an inert gas and a member selected from the group consisting of ortho-xylene and naphthalene through a catalyst A comprising a first catalytically active substance on a first porous inert carrier, said first catalytically active substance consisting essentially of 1 to 20 parts by weight of $V_2O_5$, 99 to 80 parts by weight of anatase-type $TiO_2$, and, based on the total weight of $V_2O_5$ and $TiO_2$, 0.01 to 1.0% by weight of $Nb_2O_5$, 0.5 to 1.1% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said first porous inert carrier predominantly containing SiC, and passing the thus treated gas mixture through a catalyst B comprising a second catalytically active substance on a second porous inert carrier, said second catalytically active substance consisting essentially of 1 to 20 parts by weight of $V_2O_5$, 99 to 80 parts by weight of anatase-type $TiO_2$, and, based on the total weight of the $V_2O_5$ and $TiO_2$, 0.01 to 1.0% by weight of $Nb_2O_5$, 1.2 to 2.5% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said second porous inert carrier predominantly containing SiC.

2. The method according to claim 1, wherein the volume ratio of catalyst A to the total of catalyst A plus catalyst B is from about 30 to about 70%, and the volume ratio of catalyst B to the total of catalyst A plus catalyst B is from about 70 to about 30%.

3. The method according to claim 1, wherein each of the first and second porous inert carriers contains not more than 10% by weight of aluminum, calculated as $Al_2O_3$, and contains at least 50% by weight of SiC, and has an apparent porosity of at least 10%.

4. The method according to claim 1, wherein each of the first and second porous inert carriers contains not more than 5% by weight of aluminum, calculated as $Al_2O_3$, and contains at least 80% by weight of SiC, and has an apparent porosity of 15 to 45%.

5. The method according to claim 1, wherein each of the first and second porous inert carriers is a sintered SiC having a SiC content of greater than 98% by weight and an apparent porosity of 15 to 40%.

6. A method for preparing phthalic anhydride by catalytic vapor phase oxidation of ortho-xylene or naphthalene, which comprises passing a gas mixture comprising molecular oxygen, an inert gas and a member selected from the group consisting of ortho-xylene and naphthalene through a catalyst A comprising a first catalytically active substance on a first porous inert carrier, said first catalytically active substance consisting essentially of 1 to 20 parts by weight of $V_2O_5$, 99 to 80 parts by weight of anatase-type $TiO_2$, and, based on the total weight of the $V_2O_5$ and $TiO_2$, 0.01 to 1.0% by weight of $Nb_2O_5$, 0.5 to 1.1% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said first porous inert carrier containing not more than 10% by weight of aluminum, calculated as $Al_2O_3$, and containing at least 50% by weight of SiC, and having an apparent porosity of at least 10%, at least 50% of the total pore volume of the pores of diameters less than 10 microns in the supported catalytically active substance being pores of diameters being 0.15 and 0.45 micron, and passing the thus treated gas mixture through a catalyst B comprising a second catalytically active substance on a second porous inert carrier, said second catalytically active substance consisting essentially of 1 to 20 parts by weight of $V_2O_5$, 99 to 80 parts by weight of anatase-type $TiO_2$, and, based on the total weight of $V_2O_5$ and $TiO_2$, 0.01 to 1.0% by weight of $Nb_2O_5$, 1.2 to 2.5% by weight of $P_2O_5$, 0 to 0.25% by weight of $K_2O$ and 0 to 0.5% by weight of $Cs_2O$, the total weight of the $K_2O$ and $Cs_2O$ being at least 0.05% by weight, 0.05 to 0.3% by weight of $Na_2O$ and 0 to 0.5% by weight of $Rb_2O$, said second porous inert carrier containing not more than 10% by weight of aluminum, calculated as $Al_2O_3$, and containing at least 50% by weight of SiC, and having an apparent porosity of at least 10%, at least 50% of the total pore volume of the pores of diameters less than 10 microns in the supported catalytically active substance being pores of diameters between 0.15 and 0.45 micron.

7. A method according to claim 6, wherein the volume ratio of catalyst A to the total of catalyst A plus catalyst B is from about 30 to about 70%, and the volume ratio of catalyst B to the total of catalyst A plus catalyst B is from about 70 to about 30%.

8. The method according to claim 6, wherein each of the first and second porous inert carriers contains not more than 5% by weight of aluminum, calculated as $Al_2O_3$, and contains at least 80% by weight of SiC, and has an apparent porosity of 15 to 45%.

9. The method according to claim 6, wherein each of the first and second porous inert carriers is a sintered SiC having a SiC content of greater than 98% by weight and an apparent porosity of 15 to 40%.

* * * * *